United States Patent [19]

Heiland et al.

[11] Patent Number: 4,478,096
[45] Date of Patent: Oct. 23, 1984

[54] SHIELDED SNIFFING DEVICE

[75] Inventors: Wolfgang K. Heiland, Trevose; Paul Magidman, Warrington, both of Pa.

[73] Assignee: The United States of America as represented by the Secretary of Agriculture, Washington, D.C.

[21] Appl. No.: 509,091

[22] Filed: Jun. 29, 1983

[51] Int. Cl.³ .............................................. G01N 1/24
[52] U.S. Cl. .................................. 73/864.73; 73/40.7
[58] Field of Search ................... 73/863, 864, 864.33, 73/864.34, 864.73, 40.7

[56] References Cited

U.S. PATENT DOCUMENTS

| 2,706,398 | 4/1955 | Davidson | 73/40.7 |
| 2,996,661 | 8/1961 | Roberts | 73/40.7 |
| 3,998,101 | 12/1976 | Bradshaw | 73/864 |

Primary Examiner—S. Clement Swisher
Attorney, Agent, or Firm—M. Howard Silverstein; William E. Scott; David G. McConnell

[57] ABSTRACT

A device for detecting contraband in closed luggage is provided. The device is especially useful for detecting fruits, vegetables, foodstuffs and other materials that give off carbon dioxide.

1 Claim, 8 Drawing Figures

SHIELDED SNIFFING DEVICE

BACKGROUND OF THE INVENTION

1. Field of The Invention

This invention relates to a device or apparatus for sampling the air inside closed luggage at ports of entry into the United States of America and especially to an apparatus for detecting contraband being smuggled into the country inside such luggage.

2. Description of The Art

Detection of solid materials, especially those made of metal, can in many cases be made with X-ray apparatus. However, X-ray techniques are not adequate for the detection of such items as fruits and vegetables.

SUMMARY OF THE INVENTION

An object of this invention is to provide an apparatus or device which can detect contraband inside luggage.

Another object is to provide a simple, hand-held device with which the presence or absence of contraband in luggage can be detected rapidly.

According to this invention the above objects are accomplished by a device having a handle, a body, a lower section and a spool valve. The handle is provided with a bore and with two ports, each of which is connected to the bore by a passageway. The body fits into the bore in the handle and is also provided with a bore, a multitude of axial holes for passage of gas from the bore of the handle to the lower section, and an orifice to provide access to one of the passageways in the handle. The lower section consists essentially of two half heads, a shield air guide and bearing and an axially movable nozzle and nozzle extension tube. The spool valve is movably fitted into the bore in the body and has two sets of radial holes, each of which provides communication with the orifice in the body depending on the position of the valve in the bore and with one of two orifices in the spool valve.

DESCRIPTION OF THE INVENTION

The invention is a hand held apparatus devised principally to detect and measure the level of $CO_2$ inside closed luggage. Early attempts to detect elevated levels of $CO_2$ inside closed luggage required the use of a hooded type enclosure. The enclosure was flooded with reference air so that luggage could be sampled with a crude device without interference from the $CO_2$ in the operator's breath. A system of this type is very inadequate for use at ports of entry because it is very slow and very cumbersome and cannot be relied on for a high degree of accuracy.

The apparatus or sniffing device of this invention, on the other hand, provides great mobility and speed, can be used on any size luggage, and does not require physical handling of the luggage. In fact, the detection operation can be performed while the luggage is being conveyed past an inspection station. It allows the detection of a slightly elevated $CO_2$ content over that of normal or ambient air without interference from the highly elevated $CO_2$ content of the operator's breath.

Figure 1:
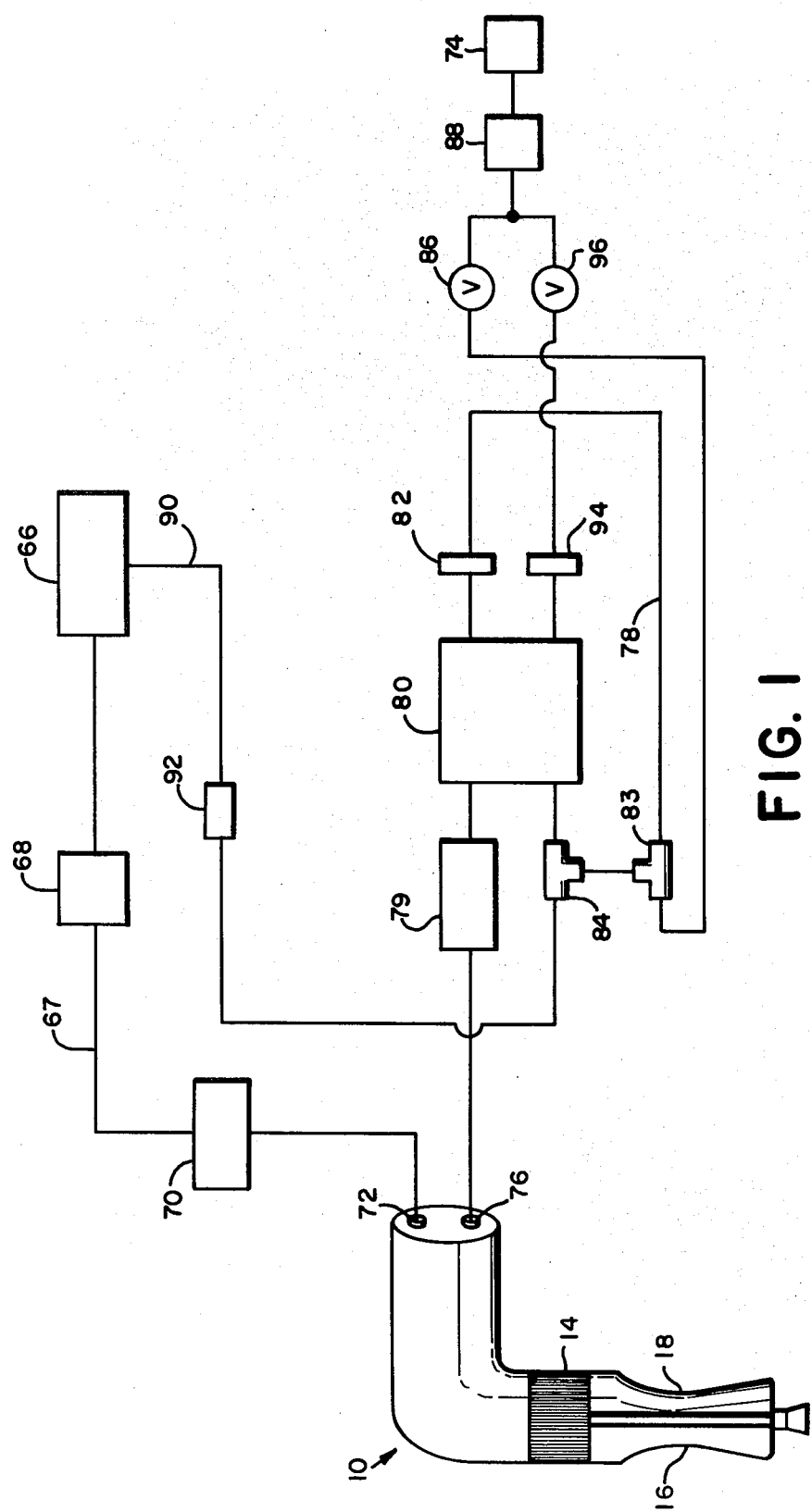
FIG. 1 is a schematic showing the sniffing device as part of a complete contraband detection arrangement.
Figure 2:
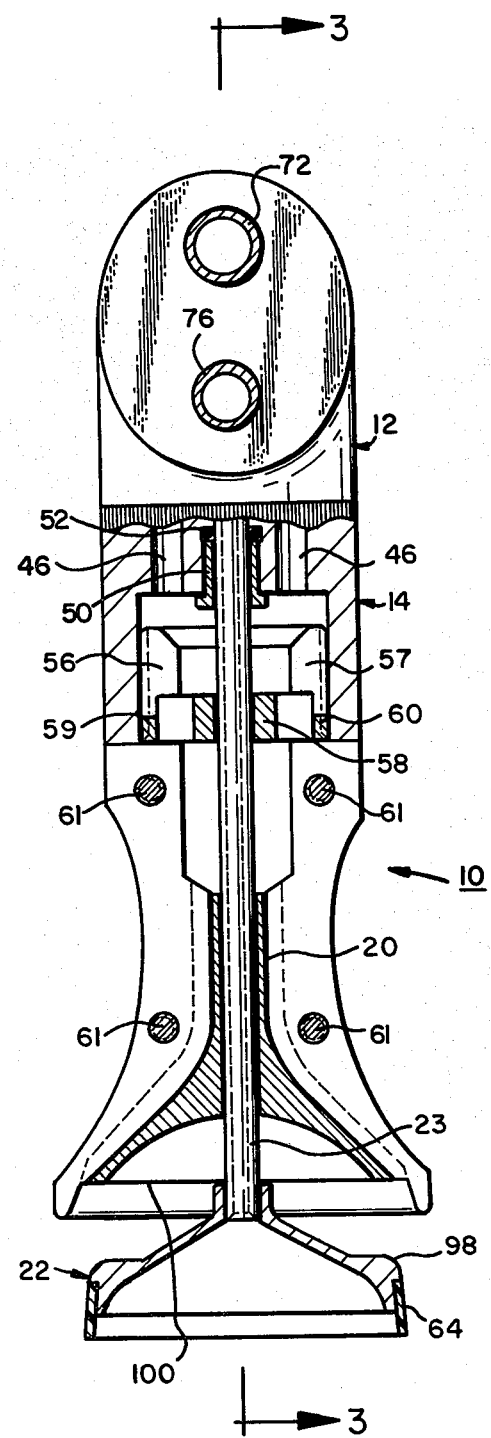
FIG. 2 is a longitudinal view, mostly in cross-section of the assembled device and shown in standby position.
Figure 3:
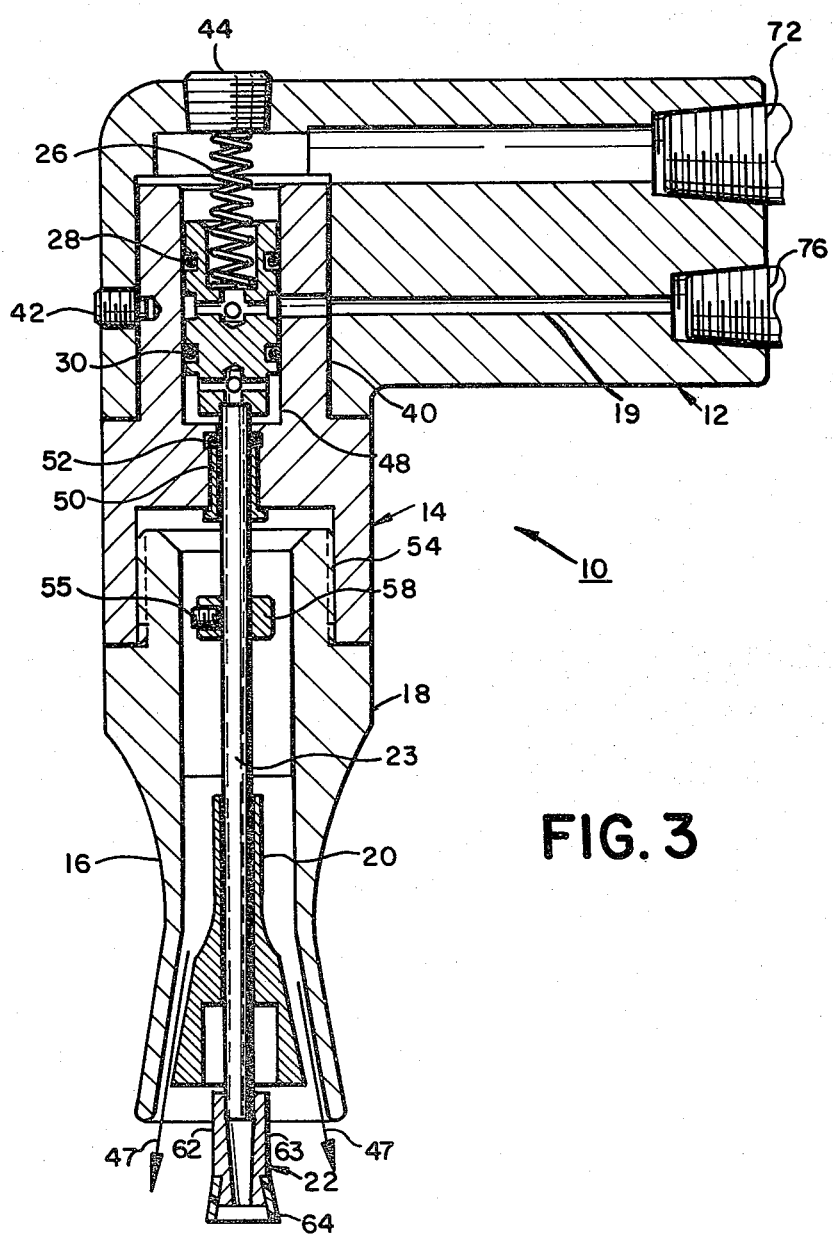
FIG. 3 is a longitudinal cross-section along line 3—3 of FIG. 2.
Figure 4:
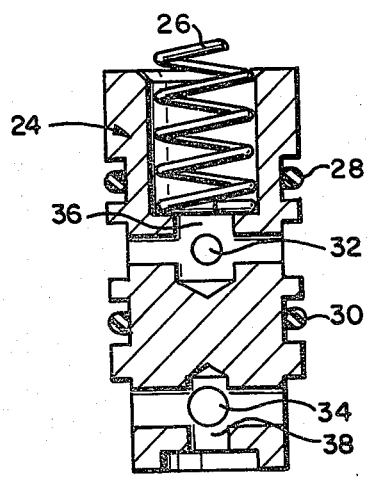
FIG. 4 is a longitudinal cross-section of the spool valve of the apparatus.
Figure 7:
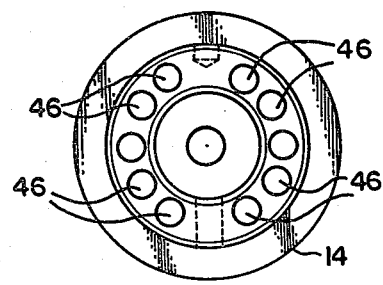
FIG. 7 is a top view of the disassembled body.
Figure 8:
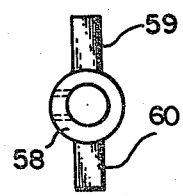
FIG. 8 is a top view of nozzle extension tube and guide.
Figure 5:
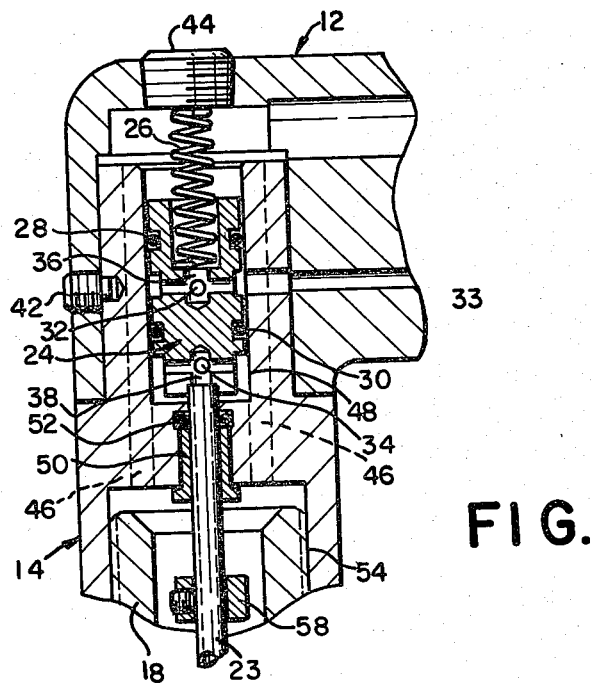
FIG. 5 is a longitudinal cross-section of the body section of the apparatus showing the position of the spool valve when the apparatus is in standby position.
Figure 6:
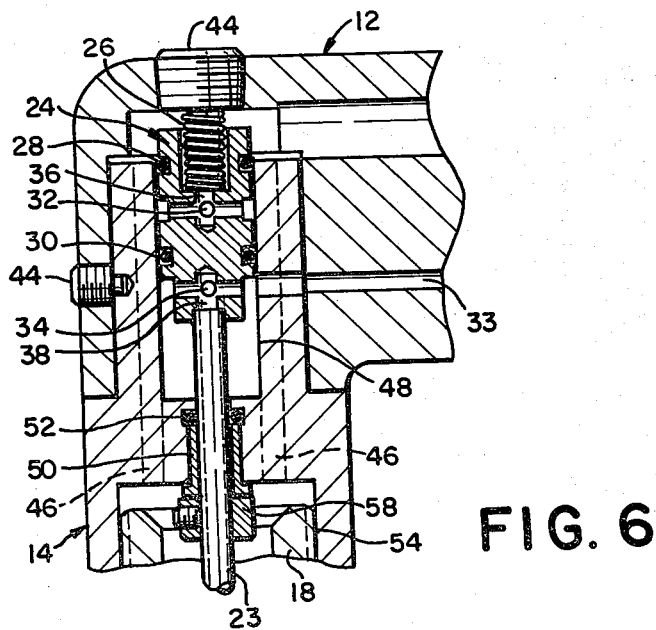
FIG. 6 is a longitudinal cross-section of the body section of the apparatus showing the position of the spool valve when the apparatus is in operating position.

The device or apparatus of this invention is used as part of a complete contraband detection system shown schematically in FIG. 1. As shown in the other drawings, especially FIGS. 2 and 3, the major components of the sniffing apparatus 10 are handle 12, body 14, and a lower section consisting essentially of two half heads 16 and 18, shield air guide and bearing 20, and nozzle 22 with extension tube 23. Spool valve 24, also shown individually in FIG. 4 and in FIGS. 5 and 6, provides a means for by-passing some shield air into the detection system. When sniffing device 10 is on standby, spool valve 24 is positioned as shown in FIG. 5, and when it is in operating position, spool valve 24 is positioned as shown in FIG. 6. Compression spring 26 is provided to keep valve 24 in the position shown in FIG. 5 when device 10 is on standby. Spool valve 24 is provided with two O-rings 28 and 30, two sets of four equally spaced radial holes, an upper set 32 and a lower set 34, and two orifices 36 and 38. Orifice 36 provides a passageway from the top of spool valve 24 to the upper set of radial holes 32, and the second orifice 38 provides a passageway from the bottom of valve 24 to the lower set of radial holes 34. Body 14 is provided with radial orifice 33 positioned to form a continuous opening with passageway 19 in handle 12 and with radial holes 32 when 10 is in a standby position, FIG. 5, and with radial holes 34 when 10 is in operating position, FIG. 6.

Handle 12 and body 14 are machined from aluminum followed by hard anodizing but they can be made of other metals or materials such as plastic. Bore 40 in handle 12 provides a slip fit with body 14 which in turn is positioned radially and axially by setscrew 42. Plug 44 centers the top end of compression spring 26. Body 14 is provided with axial holes 46 and machined bore 48 to house spool valve 24. Body 14 is also provided with bearing 50 and O-ring 52 to guide and seal the upper end of extension tube 23 of nozzle 22, and with internal threads 54 for attaching the two half heads 16 and 18.

Assembled to body 14 by means of external threads (not shown) matching internal threads 54, the two half heads 16 and 18 are provided with a pair of slots 56 and 57 for guiding the two wings 59 and 60 of nozzle guide 58 which is attached by setscrew 55 to extension tube 23. Nozzle guide 58 also limits the downward travel of nozzle 22 when the wings contact the lower end of slots 56 and 57. Shield air guide and bearing 20 is sandwiched between two half heads 16 and 18 and these three components are held together with screws 61. Thus, the combination of half heads 16 and 18 and guide 20 forms a cavity around nozzle 22 that provides a passageway for shield air to skirt nozzle 22. Half heads 16 and 18 are also made from aluminum followed by hard anodizing, while guide 20 is machined from oil impregnated sintered bronze. However, as with handle 12 and body 14, half heads 16 and 18 and guide 20 may be made from other metals or materials. Nozzle 22 is fabricated from four components. Two brass shells 62 and 63 are brazed to each other and to extension tube 23 which is made of stainless steel. Other metals and materials may also be used to make the nozzle. Rubber lip 64 around the lower end of nozzle 22 is permanently bonded to shields 62 and 63.

Device 10 is used with a system depicted schematically in FIG. 1. Ambient air which is filtered through filter 66 and pumped through hosing or tubing 67 by pressure or diaphragm pump 68 through surge tank 70 enters device 10 through port 72. Inside 10, the air passes through axial holes 46 through body 14 and out of half heads 16 and 18. At the same time when device 10 is in standby position, a small amount of the filtered ambient air does not go through axial holes 46 and is drawn by vacuum pump 74 through the coils of spring 26, orifice 36, radial holes 32, radial orifice 33, passageway 19, port 76, tubing 78, in-line filter 79, first side of differential $CO_2$ detector 80, first flow meter or rotameter 82, tee 83, to which differential flow controller 84 is connected, flow control valve 86, surge tank 88 and exhausted to the atmosphere through pump 74. Filtered air from filter 66 is also drawn by pump 74 through tubing 90, in-line filter 92, differential flow controller 84, second side of $CO_2$ detector 80, second flow meter or rotameter 94, second flow control valve 96, surge tank 88, and through pump 74 to the atmosphere. This latter airflow through the second side of detector 80 is the reference air flow for the detector. When the air flow in tubing 78 passes through tee 83 it exerts pressure on a diaphragm in differential flow controller 84 to equalize the flow rate of the reference and sample gases.

When the operator presses device 10 against the closure of a piece of luggage, nozzle 22 moves up and into guide 20 until shoulder 98 is stopped by surface 100. Pressure exerted by the operator causes rubber lip 64 on nozzle 22 to spread out and form a tight seal over the luggage closure so that ambient air which passes through axial holes 46, body 14 and half heads 16 and 18 escapes all around and away from nozzle 22. Since this ambient air shields nozzle 22 from external sources of $CO_2$ it is referred to as shield air and is depicted by number 47 in FIG. 3. At the same time extension tube 23 of nozzle 22 lifts spool valve 24 against pressure of spring 26 so that spool valve 24 is now in the position shown in FIG. 6. With valve 24 in this position, radial orifice 33 is aligned with lower radial holes 34 so that the gaseous contents of the luggage are drawn through nozzle 22, extension tube 23, orifice 38, radial holes 34, orifice 33, passageway 19, and into the detection system through port 76.

The difference in $CO_2$ content between the first and second side of detector 80 is converted into an appropriate electrical signal to scribe a line on the strip chart recorder of detector 80. While device 10 is in standby the $CO_2$ content of the sample stream is the same as that of the reference stream so the recorder scribes a baseline. An alternative to using a strip chart recorder is to use an audible or visual alarm which is activated when the $CO_2$ level in the gases being measured exceeds a predetermined amount.

The ambient air that flows over nozzle 22 and shields it from external sources of $CO_2$ flows at a rate of 25–30 liters per minute while the flow rate in the sample and reference lines, 78 and 90, respectively, is 1.5–2.0 liters per minute.

We claim:

1. A device for detecting contraband in closed luggage comprising
    (a) a handle provided with a bore and having two ports, each of which is connected to a passageway providing access to said bore;
    (b) a body, the upper part of which fits into the bore in the handle, said body being provided with a bore, a multitude of axial holes to allow passage of gas through the body, and an orifice, said orifice providing access from the bore to one of the passageways in the handle;
    (c) a spool valve movably located in the bore of the body and having two sets of radial holes for alignment with the orifice in the body when the spool valve is in either of two positions and two orifices, each orifice providing a passageway to one of the two sets of radial holes; and
    (d) a lower section consisting essentially of two half heads, a shield air guide and bearing and a nozzle with an extension tube, said lower section being threaded on to the body and said nozzle and extension tube being provided with means for moving axially within the lower section and the body.

* * * * *